US00PP35406P2

(12) United States Plant Patent
Byington

(10) Patent No.: US PP35,406 P2
(45) Date of Patent: Oct. 3, 2023

(54) SHRUB ROSE PLANT NAMED 'BYIBLOOMTHYME'

(50) Latin Name: *Rosa hybrida*
Varietal Denomination: BYIbloomthyme

(71) Applicant: Teresa Byington, Brownsburg, IN (US)

(72) Inventor: Teresa Byington, Brownsburg, IN (US)

( * ) Notice: Subject to any disclaimer, the term of this patent is extended or adjusted under 35 U.S.C. 154(b) by 0 days.

(21) Appl. No.: 17/803,755

(22) Filed: Nov. 10, 2022

(51) Int. Cl.
*A01H 5/02* (2018.01)
*A01H 6/74* (2018.01)

(52) U.S. Cl.
USPC ..... Plt./107
CPC ..... *A01H 6/749* (2018.05)

(58) Field of Classification Search
USPC ..... Plt./101, 102, 107
See application file for complete search history.

*Primary Examiner* — Karen M Redden

(57) ABSTRACT

'BYIbloomthyme' is a new and distinct cultivar of *Rosa hybrida* having a mounded, well-branched, compact plant habit; vigorous growth; double flowers typically borne in clusters of 3 or more; light peach-pink petal color; continuous flowering throughout the growing season; resistance to major fungal diseases; and ability to root and grow vigorously from softwood and semi-hardwood cuttings.

4 Drawing Sheets

Latin name of the plant claimed: *Rosa hybrida.*
Variety denomination: 'BYIbloomthyme'.

BACKGROUND OF THE INVENTION

This invention relates to a new and distinct variety of shrub rose. The varietal denomination of the new variety is 'BYIbloomthyme'. It was discovered as a naturally occurring mutation of the cultivar 'ZLEMarianneYoshida' (U.S. Plant Pat. No. 22,205) growing in a sunny garden bed in Brownsburg, Ind. during the spring of 2019. A section of a plant of 'ZLEMarianneYoshida' produced blooms that were light peach-pink in color versus the darker peach-pink color that is characteristic of 'ZLEMarianneYoshida'. New stems from the mutated section of 'ZLEMarianneYoshida' continued to produce light peach-pink blooms. Stem cuttings were taken from the mutated portion of the plant in September 2019 and the new plants generated from those cuttings continued to produce flowers with light peach-pink bloom color. In subsequent clonal generations to date, the light peach-pink bloom color of 'BYIbloomthyme' has been stable.

BRIEF SUMMARY OF THE INVENTION

The objective of isolating and propagating the stable light peach-pink flower color mutant genotype of 'ZLEMarianneYoshida' was substantially achieved, along with maintaining the desirable growth habit and all the other valuable characteristics of 'ZLEMarianneYoshida'. This is evidenced by the following unique combination of characteristics that are outstanding in the new variety and that distinguish it from 'ZLEMarianneYoshida', as well as from all other varieties of which I am aware:

1. Mounded, well-branched, compact plant habit;
2. Vigorous growth;
3. Double flowers typically borne in clusters of 3 or more;
4. Light peach-pink petal color;
5. Continuous flowering throughout the growing season;
6. Resistance to major fungal diseases;

7. Ability to root and grow vigorously from softwood and semi-hardwood cuttings.

Asexual reproduction of this new variety by rooting softwood and semi-hardwood cuttings, as performed at River Falls, Wis., shows that the foregoing and all other characteristics and distinctions come true to form and are established and transmitted through succeeding propagations.

Comparison with Parent

'BYIbloomthyme' has double light peach-pink flowers which differs from the cultivar from which it mutated or sported, 'ZLEMarianneYoshida'. 'ZLEMarianneYoshida' has double blooms with a noticeably darker peach-pink flower color. Both roses have a mounded, well-branched, compact plant habit, have blooms borne in clusters, and are resistant to common fungal diseases. 'BYIbloomthyme' differs from the female parent of 'ZLEMarianneYoshida', 1G15 (unpatented proprietary shrub rose seedling), in that 1G15 has double red blooms and a narrow, upright plant habit. 'BYIbloomthyme' differs from the male parent of 'ZLEMarianneYoshida', 1B30 (unpatented proprietary shrub rose seedling), in that 1B30 has non-recurrent flowering (typically 4-6 weeks of flowering in late spring to early summer) and 'BYIbloomthyme' is continuously flowering during the growing season. In addition, the plant and flower size of 1B30 is larger than 'BYIbloomthyme'. 'BYIbloomthyme', 'ZLEMarianneYoshida', 1G15, and 1B30 have all proven to be reliably crown hardy in River Falls, Wis. in United States Department of Agriculture cold hardiness zone 4. 'BYIbloomthyme' and 'ZLEMarianneYoshida' have also proven to be reliably crown hardy in Brownsbury, Ind. which is in United States Department of Agriculture cold hardiness zone 6.

Comparison with Similar Variety

The rose variety with the greatest similarity to 'BYIbloomthyme' is 'ZLEMarianneYoshida' (marketed under the names Oso Easy® Petit Pink and Oso Happy® Petit Pink; U.S. Plant Pat. No. 22,205), a rose of the shrub commercial class. Both 'BYIbloomthyme' and 'ZLEMarianneYoshida' have double blooms borne in clusters, comparable plant habits, and are resistant to common fungal diseases. The key difference is that 'BYIbloomthyme' has blooms that are a light peach-pink color and 'ZLEMarianneYoshida' has blooms that are a darker peach-pink color.

BRIEF DESCRIPTION OF THE DRAWINGS

The accompanying illustration shows typical specimens of the vegetative growth and flowers of this new variety in different stages of development, depicted in color as nearly true as it is reasonably possible to make the same in a color illustration of this character.

DETAILED BOTANICAL DESCRIPTION

Figure 1:
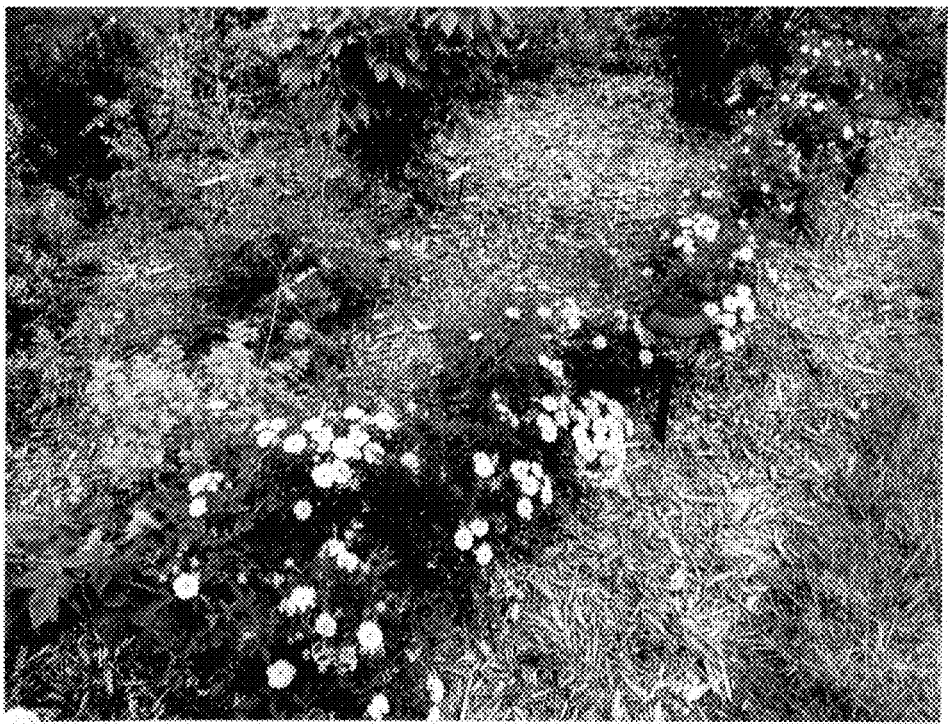
FIG. 1 illustrates a row of maturing plants in their second growing season (August 2022) in a garden border.
Figure 2:
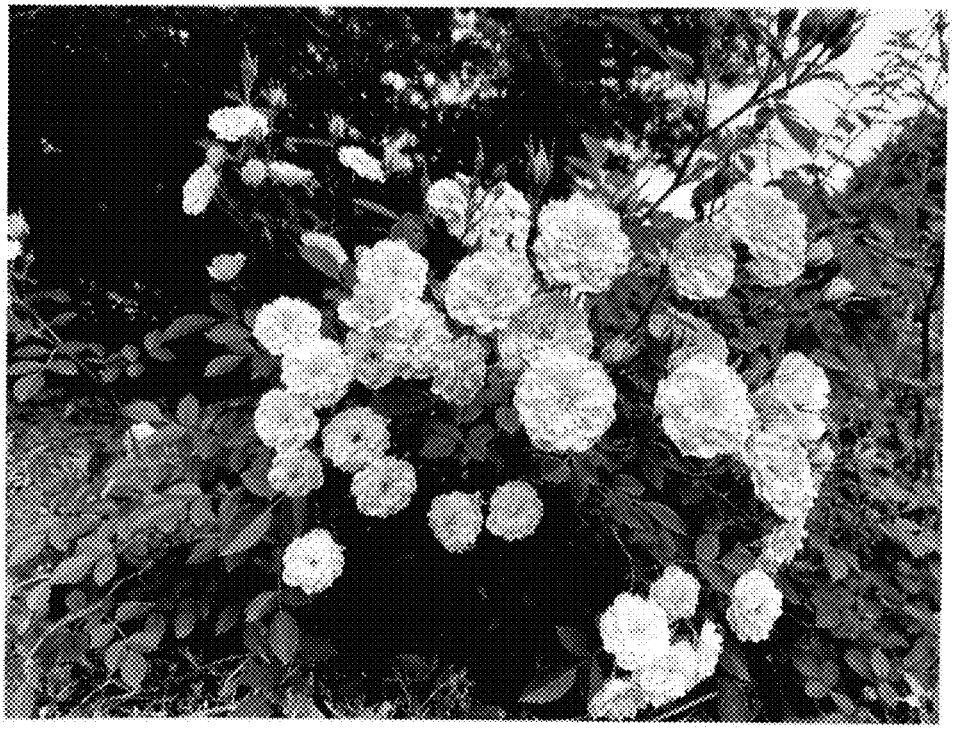
FIG. 2 illustrates blooms at multiple stages of opening.
Figure 3:
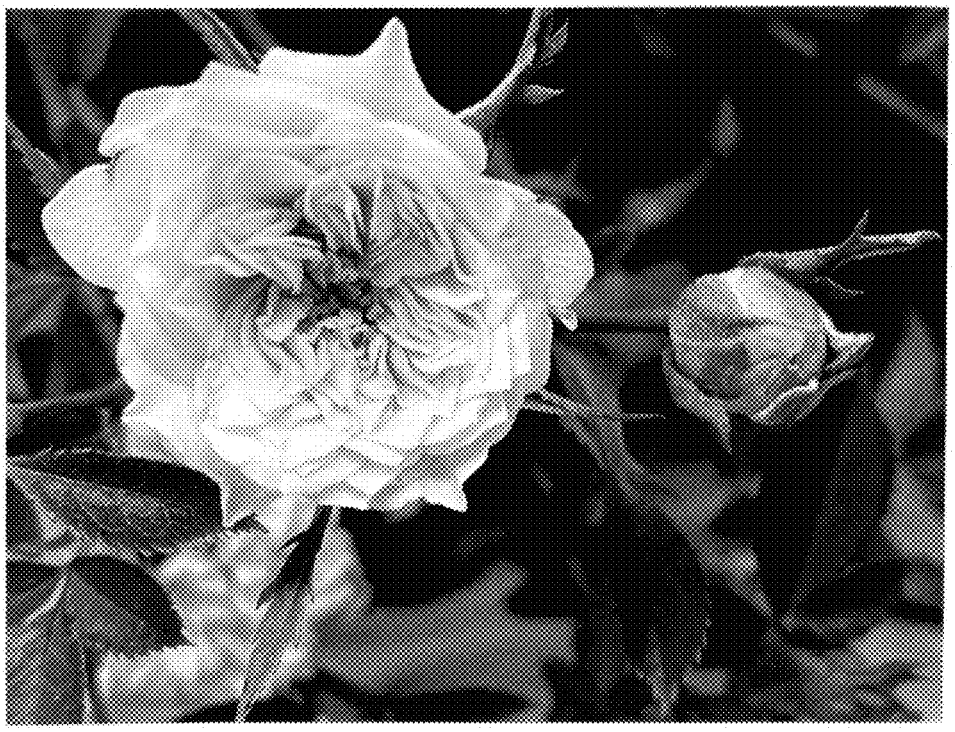
FIG. 3 illustrates a close-up view of a near fully-open flower and a flower bud just starting to open.
Figure 4:
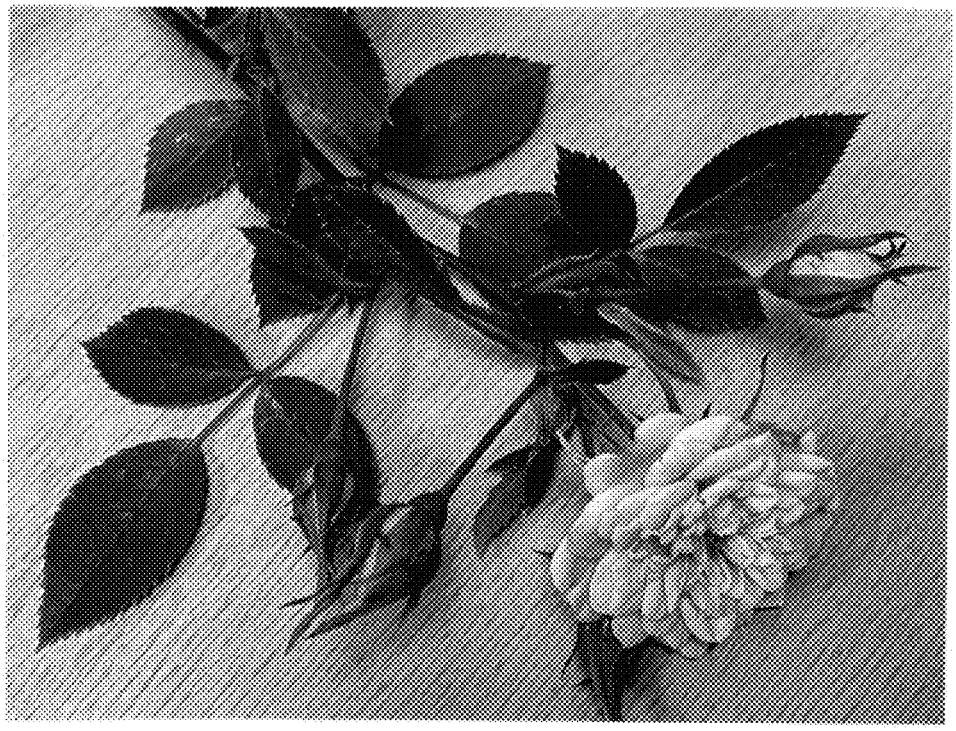
FIG. 4 illustrates leaves and flowers on a typical stem.
Figure 5:
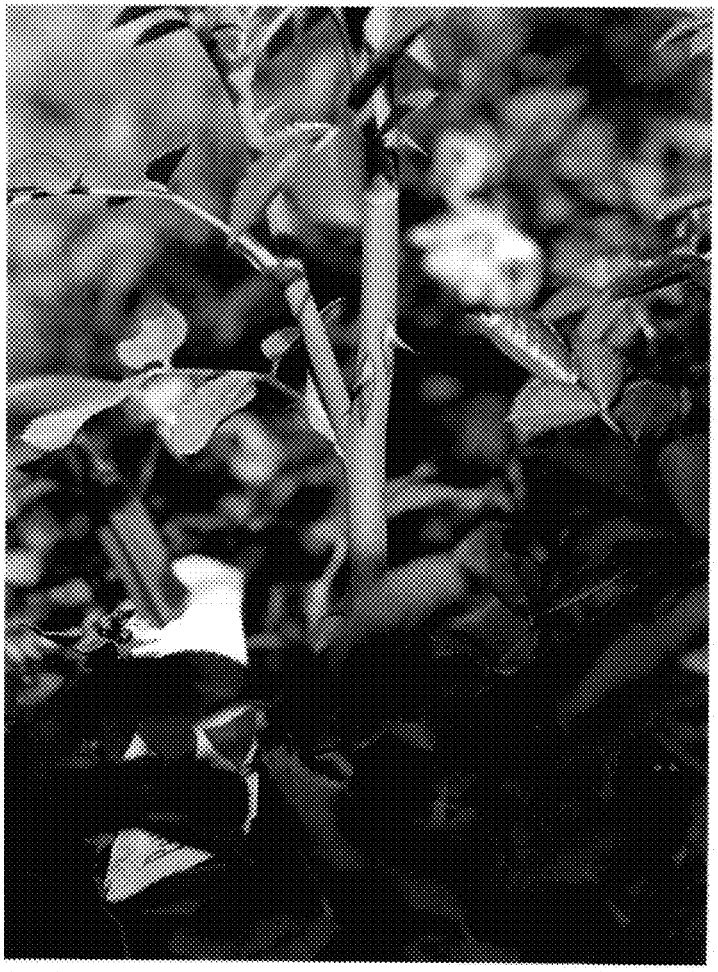
FIG. 5 illustrates prickles on a typical stem.
Figure 6:
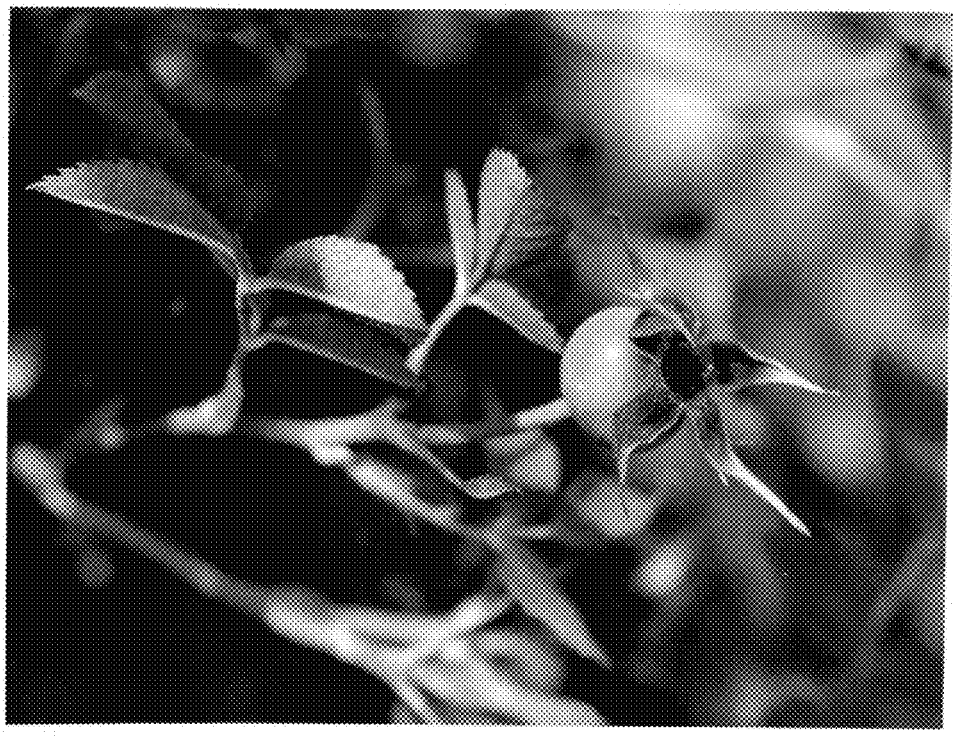
FIG. 6 illustrates a maturing hip.

The following is a detailed description of my new rose cultivar with color descriptions using terminology in accordance with The Royal Horticultural Society (London) Colour Chart (2015), except where ordinary dictionary significance of color is indicated. The phenotype of the new cultivar may vary with differences in environmental, climatic, and cultural conditions, as it has not been tested under all possible environmental conditions. Descriptions are based on observations of plants approximately one year of age that were propagated from semi-hardwood cuttings and are not grafted onto rootstock.

Parentage:

*Originating parent.*—'BYIbloomthyme' is a light peach-pink flowering mutation of the darker peach-pink flowered rose 'ZLEMarianneYoshida'.

Classification:

*Botanical.*—*Rosa hybrida.*

*Commercial.*—Shrub.

Flower:

Blooming habit: Continuous.

Bud:

*Size.*—12-16 mm long and 10-11 mm in diameter when the petals start to unfurl.

*Form.*—The bud form is ovoid and pointed.

*Color.*—When sepals first divide, visible petal color is Orange Group 25C. When half blown, the upper or adaxial sides of the petals are closest to Red Group 36C on the distal end and Orange Group 29D at the proximal end. The lower or abaxial sides of the petals have a background color of Red Group 38C with small (≤2 mm wide and long) striations of Red Group 49A. The base or proximal end of the petals (<2 mm) are Yellow-Orange Group 16C.

*Sepals.*—Color: Green Group 137C on the abaxial side and Green Group 138C on the adaxial side. Length: 11-16 mm. Width: 4-6 mm. Shape: ovate to oblong with acuminate tips. Surface texture: Adaxial, Hoary. Abaxial, Generally smooth with some very small glandular hairs (<0.2 mm). There are three lightly appendaged sepals. There are two unappendaged sepals which have hoary edges.

*Receptacle.*—Color: Yellow-Green Group 144B. Shape: round to slightly elliptic. Size: Small, about 4-5 mm wide and 5-6 mm long. Surface: primarily glabrous sometimes with very small glandular hairs (<0.2 mm).

*Peduncle.*—Length: Medium, averaging about 10-20 mm. Surface: primarily glabrous sometimes with very small glandular hairs (<0.2 mm). Color: Yellow-Green Group 144C. Strength: Stiff, primarily erect.

Bloom:

*Size.*—Small. Typical open diameter is 29-36 mm.

*Borne.*—Typically in clusters of 3 or more blooms per stem.

*Stems.*—Strength: Strong. Length: Typically about 20-30 cm. Stem diameter: Varies and is typically 3-6 mm. Larger stems arising from the base of the plant are about 0.3-0.6 cm in diameter, while smaller stems arising from either the base of the plant or secondary or tertiary stems arising within the plant canopy are typically 2-5 mm in diameter.

*Form.*—When blooms first open: High centered with petals unfurling in a symmetrical manner that is commonly called exhibition form by rose growers and exhibitors. When blooms fully open: Slightly cupped to flat.

*Permanence.*—Blooms retain their form to the end.

*Petalage.*—Double blooms with petals and petaloids typically totaling 50-80.

*Color.*—The adaxial sides of the petals is between Red Group 37C and Red Group 37D throughout most of the petal and Red Group 36C at the base or proximal end of the petal. The color of the abaxial side of the petals is primarily Red Group 39D with darker striations (<2 mm in length and width) of Red Group 49A.

*Discoloration.*—The general tonality of the adaxial petal surface of a fully open bloom at the first day through the third day: Orange Group 28B. The general tonality of the adaxial petal surface at day eight: Red Group 36B. The background color of the abaxial surface of the petal is Orange Group 29C with small (≤2 mm wide and long) striations of Red Group 54C typically for the first three days and then by day eight the background color is Red Group Red Group with small (≤2 mm wide and long) striations of Red Group-55B.

*Fragrance.*—Slight. Character of fragrance: Damask to spicy.

Petals:

*Texture.*—Thick and satiny to the touch.

*Length.*—1.3-1.6 cm.

*Width.*—The outermost petals of the bloom tend to be wider and are typically 1.1-1.6 cm and the innermost petaloids are more narrow and are typically 0.5 cm.

*Shape.*—The outermost petals are obcordate and the shape of the petaloids transitions moving towards the center of the flower to obovate and then finally oblong.

*Margin.*—Entire.

*Apex shape.*—Obcordate and sometimes with a small acuminate point (≤1 mm) in the axis for the outermost petals and rounded for the petals towards the center of the bloom.

*Base shape.*—Rounded for the outermost petals and transitioning to cuneate for the inner petals.

*Form.*—Flat to slightly cupped.

*Arrangement.*—Multiple rows of overlapping petals.

*Petaloids.*—Roses have five true petals (except for *Rosa sericea* which typically has four) and all additional petal-like appendages are botanically petaloids. Petaloids are stamens, or in some cases also pistils, that develop into petal-like structures. However, petaloids that do not have obvious remnant stamen development are often called petals in common vernacular in United States Plant Patents and the popular press. 'BYIbloomthyme', like typical roses, has five true petals, frequently has between 42-72 petaloids that look like a typical petal, and often 2-12 petaloids that have some visible stamen development typically seen as a single anther along one of the edges of a relatively narrow petal-like structure. The petaloids with anthers attached are found at the transition area in the bloom between the most petal-like petaloids and the stamens. Pistils of 'BYIbloomthyme' have not been observed to develop into petaloids. The size and color of the attached anthers on petaloids for 'BYIbloomthyme' varies, but is comparable what is documented later for anthers. Additionally, the color of the petal-like portion of the petaloid is typical for the color of a true petal or a more petal-like petaloid without visible anther development.

*Persistence.*—Petals typically drop off cleanly before drying.

*Lastingness.*—On the plant: Long (about 8-10 days). As a cut flower: Moderate (about 7 days).

Reproductive parts:

*Stamens.*—Number per flower: 20-34. Anthers — Size: Length before dehiscence: 1.5-2.0 mm, Width before dehiscence: 1.0-1.5 mm. Length after dehiscence: 1.0 mm. Width after dehiscence: 0.8-1.0 mm. Color: Before dehiscence: Yellow Orange Group 17B. After dehiscence: Yellow-Orange Group 22A. Arrangement: Regular around styles. Filaments — Size: Length: 2-5 mm. Width: 0.25 mm. Color: Yellow-Orange Group 21A. Pollen — Color: Yellow Orange Group 17B.

*Pistils.*—Number per flower: 19-30. Styles — Color: Red Group 51A. Length: 4-6 mm. Stigmas — Color: White Group 155C. Ovary — Color of immature ovary: Yellow-White Group 158A.

*Hips.*—The fleshy portion of rose hips is hypanthium tissue and inside that tissue are achenes — single-seeded fruits with a hard pericarp surrounding the embryo. Hips are rarely observed on 'BYIbloomthyme'. For those that are present sepals persist and are present upon ripening. Hypanthium: Color immature: Green Group 146A. Color mature: Orange Group N25A. Shape: Generally round. Size: 10-18 mm long and 10-18 mm wide.

*Achenes (ripe).*—Color: Yellow Green Group 150D. Shape: Irregular since they press up against each other and the hypanthium wall tightly. Size: 4-7 mm. Typically there are 1-3 achenes per hip.

Plant:

*Form.*—Rounded bush.

*Growth.*—Very vigorous, well-branched, and dense.

*Age at maturity.*—3 years.

*Mature plant.*—Height is 60 cm and width is 75 cm.

Leaf:

*Form.*—Leaves typically have five or seven leaflets on a typical leaf.

*Arrangement.*—Leaves are alternately arranged on stems.

*Size.*—Medium (6-9 cm long and 4-5 cm wide).

*Quantity.*—Normal.

*Leaflet color.*—New foliage: Adaxial side: Yellow-Green Group 146A and where full sun hits the new foliage there is a light overlay of Red-Purple Group 59B. Abaxial side: Yellow Green Group 146B. Old foliage: Adaxial side: Green Group 137B. Abaxial side: Green Group 138B.

*Leaflet venation pattern.*—Pinnate reticulate.

*Leaflet venation color.*—The color of the veins is the same or very close to that of the overall leaf blade. New foliage: Adaxial side: Yellow-Green Group 146A and where full sun hits the new foliage there is a light overlay of Red-Purple Group 59B. Abaxial side: Green Group 138B. Old foliage: Adaxial side: Green Group 137B. Abaxial side: Green Group 138B.

*Leaflet size.*—Terminal leaflets: Medium (2.3-3.0 cm long and 1.5-2.0 cm wide). Non-terminal leaflets: Medium (1.8-2.3 cm long and 1.2-1.7 cm wide).

*Leaflet shape.*—Ovate.

*Leaflet base shape.*—Obtuse to rounded.

*Leaflet apex shape.*—Acute to slightly acuminate.

*Leaflet texture.*—Semi-glossy, rugose. On the adaxial side of leaflets the veins are slightly recessed and on the abaxial side they are slightly elevated relative to the general leaf blade.

*Leaflet edge.*—Serrated with small single serrations (about 1 mm).

*Petiole.*—Color — Yellow-Green Group 144B.

*Petiole rachis.*—Color: Green Group 138B and sometimes with Greyed-Red Group 178C highlights on especially the adaxial side.

*Petiole underside.*—Generally smooth with small prickles (1-2 mm in length and <0.3 mm in width). Prickles typically are Greyed-Red Group 181C in color.

*Fall foliage color.*—Color: Yellow Group 13A throughout the whole leaf — adaxial and abaxial sides of the leaflets, rachis, and stipules.

*Stipules.*—Short (about 1.0-1.3 cm in length). Color: Yellow-Green Group 146C, edges with several relatively parallel and very narrow appendages (0.3-0.5 mm long and 0.1 mm wide).

*Disease resistance.*—Resistant to powdery mildew (*Podosphaera pannosa*), black spot (*Diplocarpon rosae*), and rust (*Phragmidium tuberculatum*) under normal growing conditions.

*Pest persistence.*—Not observed.

Wood:

*New wood.*—Color: Generally Yellow-Green Group 146C with areas of Greyed-Red Group 178B overlaid especially if grown in high light. Bark: Smooth.

*Old wood.*—Color: Yellow-Green Group 146A. Bark: Smooth.

Typical stem prickles:

*Quantity.*—Relatively few to typical with 8-9 typically on a 15 cm length of stem.

*Form.*—Straight to slightly downward hooked.

*Length.*—4-7 mm.

*Width.*—1-2 mm near stem and narrowing to tip.

*Color when young.*—Greyed-Red Group 178A.

*Color when mature.*—Greyed-Yellow Group 161D.

Small, secondary stem prickles:

*Quantity.*—None.

Cytology:

*Ploidy.*—Triploid (2n=3x=2l). Meristematic root tip cells in the stage of metaphase of mitosis were observed to have 21 chromosomes under a light microscope at 400× magnification.

Winter hardiness: Consistently crown hardy to United States Department of Agriculture cold hardiness zone 4.

I claim:

1. A new and distinct variety of rose plant of the shrub class named 'BYIbloomthyme', substantially as herein shown and described, characterized particularly by its mounded, well-branched, compact plant habit; vigorous growth; double flowers typically borne in clusters of 3 or more; light peach-pink petal color; continuous flowering throughout the growing season; resistance to major fungal diseases; and ability to root and grow vigorously from softwood and semi-hardwood cuttings.

* * * * *